United States Patent
Güthner et al.

(12)

(10) Patent No.: US 6,841,672 B2
(45) Date of Patent: Jan. 11, 2005

(54) METHOD FOR PRODUCING 4-METHYL PYRIMIDINE

(75) Inventors: Thomas Güthner, Trostberg (DE); Bernhard Graml, Garching (DE)

(73) Assignee: Degussa AG, Trostberg (DE)

( * ) Notice: Subject to any disclaimer, the term of this patent is extended or adjusted under 35 U.S.C. 154(b) by 43 days.

(21) Appl. No.: 10/451,092

(22) PCT Filed: Jul. 25, 2001

(86) PCT No.: PCT/EP01/08614

§ 371 (c)(1),
(2), (4) Date: Jun. 18, 2003

(87) PCT Pub. No.: WO03/010151

PCT Pub. Date: Feb. 6, 2003

(65) Prior Publication Data

US 2004/0044209 A1 Mar. 4, 2004

(51) Int. Cl.⁷ ............................................. C07D 239/26
(52) U.S. Cl. ...................................................... 544/242
(58) Field of Search ......................................... 544/242

(56) References Cited

FOREIGN PATENT DOCUMENTS

| DE | 822 086 | * | 8/1949 |
|---|---|---|---|
| DE | 822 086 | C | 10/1951 |
| DE | 43 08 073 | A | 9/1994 |
| DE | 100 02 835 | C | 12/2001 |
| JP | 49124081 | A2 | 11/1974 |
| JP | 08198858 | A2 | 8/1996 |
| SU | 91 299 | A | 7/1975 |

OTHER PUBLICATIONS

Bredereck, Hellmut et al, Chem. Ber., vol. 90, pp. 942–952, 1957).*

* cited by examiner

*Primary Examiner*—Thomas McKenzie
(74) *Attorney, Agent, or Firm*—Fulbright & Jaworski L.L.P.

(57) ABSTRACT

A process is described for preparing 4-methylpyrimidine by reacting a 4,4-dialkoxy-2-butanone with a formamidine salt, optionally in the presence of a solvent or diluent, at temperatures of from 80 to 180° C. In this way, 4-methylpyrimidine can be obtained in a substantially simpler manner and at the same time in higher yields than are possible by means of existing processes.

9 Claims, No Drawings

METHOD FOR PRODUCING 4-METHYL PYRIMIDINE

This application is a 371 of PCT/EP01/08614 filed Jul. 25, 2001.

The present invention relates to a process for preparing 4-methylpyrimidine which is a viable intermediate for producing drugs and crop protection agents.

The preparation of 4-methylpyrimidine is known in principle. Aside from a number of very complicated indirect syntheses from chlorinated 4-methylpyrimidines by reduction, processes in which a $C_4$ component is reacted with an NCN component are particularly suitable for the preparation.

Bredereck et al. (Org. Synth. Coll. Vol. V, 794, Wiley 1973) describe a practicable process starting from formamide and 4,4-dimethoxy-2-butanone, in which 4-methylpyrimidine is obtained in a yield of from 54 to 63%. However, a disadvantage of this process is that a very large excess of formamide (over 6 mol of formamide per mole of 4,4-dimethoxy-2-butanone) is required. A portion of this formamide decomposes in the course of the reaction to carbon monoxide, which presents handling problems. Owing to its solubilizing properties, the remainder of the formamide hinders the subsequent extraction of the product from water. In addition, the reaction described requires very high temperatures (from 180 to 190° C.), which leads to increased by-product formation.

The only existing alternative direct synthesis is the reaction described in DE patent 822 086 of formamidine hydrochloride with the commercially unavailable 1,1,3,3-tetramethoxybutane and methanolic HCl.

It is an object of the present invention to provide a process which can be carried out in a technically simple manner for preparing 4-methylpyrimidine, which does not have the disadvantages of the prior art detailed, but instead delivers good yields from industrially available raw materials under comparatively mild reaction conditions.

According to the invention, this object was achieved by reacting a 4,4-dialkoxy-2-butanone with a formamidine salt, optionally in the presence of a solvent or diluent, at temperatures of from 80 to 180° C. In this context, it has surprisingly proven to be the case that 4-methylpyrimidine can be obtained with the aid of the process according to the invention in a substantially simpler manner and at the same time in higher yields than is possible by means of existing processes.

In the process according to the present invention, a 4,4-dialkoxy-2-butanone as a $C_4$ component is thus reacted with a formamidine salt as an NCN component.

Examples of particularly suitable 4,4-dialkoxy-2-butanones are 4,4-dimethoxybutanone and 4,4-diethoxy-2-butanone, and the industrially readily available 4,4-dimethoxy-2-butanone is to be regarded as particularly preferred.

Examples of suitable formamidine salts are appropriate salts of carboxylic acids, hydrohalic acids or oxygen acids and in particular the acetate, the hydrochloride and the sulfate. These formamidine salts can be prepared in a technically simple manner, for example formamidine acetate (cf. DE-B 38 08 767).

These two starting substances can be reacted with or without solvent or diluent (for example alcohols, esters or carboxylic acids) and also with or without further substances, for example catalysts (in particular acids or acidic salts). However, preference is given to carrying out the reaction without solvent or addition of further substances.

The molar ratio of the 4,4-dialkoxy-2-butanone to formamidine salts is preferably between 1:2 to 2:1, in particular 1.2:1 to 1:1.2. The starting compounds may be initially charged together, although it is possible without any problem to meter in one of the two starting components during the reaction.

The reaction according to the invention is carried out at temperatures of from 80 to 180° C., preferably from 110 to 150° C. Alcohol formed, for example methanol or ethanol, can be refluxed. However, in a preferred embodiment, it is continuously removed from the reaction mixture by distillation. The reaction time is generally from 0.5 to 48 hours, preferably from 2 to 8 hours.

After reaction is complete, the reaction mixture is preferably cooled, admixed with water and a strong base, for example sodium hydroxide solution, and the 4-methylpyrimidine is extracted in a known manner using an organic solvent (for example t-butyl methyl ether) and the 4-methylpyrimidine is purified by distillation after removing the solvent, the purification preferably being carried out with the aid of fractional distillation.

The process according to the invention enables 4-methylpyrimidine to be obtained in a technically simple manner in good yields and high purities, starting from industrially available starting materials.

The examples which follow are intended to illustrate the present invention in detail.

EXAMPLES

Example 1
(Comparison According to Bredereck et al)

200 g (1.5 mol) of 4,4-dimethoxy-2-butanone, 375 g (8.3 mol) of formamide, 25 g of ammonium chloride and 12.5 g of water were initially charged in a three-neck flask equipped with a column and Liebig condenser, heated to 185° C. (bath temperature) within 1 hour and maintained at this temperature over 5 hours. During this time, a liquid distilled over from the top of the column at a top temperature of from 50 to 65° C., and contained methanol, methyl formate and ammonia and released carbon monoxide over several days.

The viscous reaction product was admixed with 500 ml of water and 65 g of 50% sodium hydroxide solution and then extracted with t-butyl methyl ether in a liquid-liquid extractor for 26 hours.

The extract was concentrated and the crude product (71.5 g) was distilled through a column to obtain two fractions:

|  | Top temperature | Weight | 4-methylpyrimidine content |
| --- | --- | --- | --- |
| Fraction 1 | 140–142° C. | 41.5 g | 97.5% |
| Fraction 2 | 142–144° C. | 8.5 g | 88.3% |

The total isolated yield was calculated as 34.0%.

Example 2
(Inventive)

198.2 g (1.5 mol) of 4,4-dimethoxy-2-butanone were initially charged in a three-neck flask equipped with a column and Liebig condenser and heated to 140° C. To this mixture were added in 10 equal portions 141.9 g (1.36 mol) of formamidine acetate over the course of one hour. During this time and also during the 4-hour post-reaction time at 140° C., pure methanol distilled off continuously.

The mixture was cooled, admixed with 100 g of water and 65 g of 50% sodium hydroxide solution, and extracted continuously with t-butyl methyl ether for a total of 20 hours.

The extract was concentrated and the crude product (101.8 g) distilled through a column to obtain two fractions:

|  | Top temperature | Weight | 4-methylpyrimidine content |
| --- | --- | --- | --- |
| Fraction 1 | 140–142° C. | 68.5 g | 96.1% |
| Fraction 2 | 142–144° C. | 14.0 g | 94.4% |

The total isolated yield was calculated as 61.8%.

Example 3

(Inventive)

208.2 g (2.0 mol) of formamidine acetate was suspended in 100 g of pure acetic acid and heated to 80° C. Within 2 hours, 198.2 g (1.5 mol) of 4,4-dimethoxy-2-butanone were metered in at 80° C. and subsequently heated to 150° C. (bath temperature) for a further 3 hours. Over the entire reaction time, methanol formed was continuously distilled off.

The mixture was cooled, admixed with 300 g of water and 165.5 g of 50% sodium hydroxide solution and extracted continuously with t-butyl methyl ether for a total of 20 hours.

The extract was concentrated and the crude product (90.3 g) distilled through a column. 72.8 g of 4-methylpyrimidine having a purity of 95.3% were obtained. The yield was 49.0%.

What is claimed is:

1. A process for preparing 4-methylpyrimidine comprising reacting a 4,4-dialkoxy-2-butanone with a formamidine salt, optionally in the presence of a solvent or diluent, at temperatures of from 80 to 180° C.

2. The process of claim 1, wherein said 4,4-dialkoxy-2butanone is 4,4-dimethoxy-2-butanone.

3. The process of claim 1, wherein said formamidine salt is formamidine acetate.

4. The process of claim 1, wherein the reaction is carried out at a temperature of from 110 to 150° C.

5. The process of claim 1, wherein the moltar ratio of 4,4-dialkoxy-2-butanone to formamidine salt is from 1:2 to 2:1.

6. The process of claim 1, wherein the molar ratio of 4,4-dialkoxy-2-butanone to formadine salt is from 1.2:1 to 1:1.2.

7. The process of claim 1, wherein alcohol formed during the reaction is continuously distilled off.

8. The process of claim 1, wherein after the reaction is completed, the reaction mixture is admixed with water and a strong base solution and 4-methylpyrimidine is extracted with an organic solvent and subsequently purified by distillation.

9. The process of claim 8, wherein said distillation is fractional distillation.

\* \* \* \* \*